United States Patent [19]

Kirsch

[11] Patent Number: Plant 6,176

[45] Date of Patent: May 10, 1988

[54] LILY PLANT NAMED SNOW PRINCE

[75] Inventor: Ted T. Kirsch, Myrtle Point, Oreg.

[73] Assignee: Melridge Inc., Gresham, Oreg.

[21] Appl. No.: 861,247

[22] Filed: May 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; W. Dennis Drehkoff

[57] ABSTRACT

A new and distinct lily cultivar of the Oriental hybrid type characterized by very large, pure white, bowl-shaped flowers having broad tepals of thick substance and borne as a compact raceme on strong, unusually thick stems and flowering profusely in midseason for Oriental lilies. This plant has abundant foliage, a vigorous growth habit, and is capable of being forced for potted plant cultivars.

1 Drawing Sheet

BACKGROUND OF THE INVENTION

This new variety of lily plant originated as a seedling of unknown parentage discovered by me at my nursery in Arcata, Calif. Its large and pure white flowers in combination with its apparently vigorous growth habit prompted me to propagate this discovery for further evaluation. This plant was propagated by me and under my direction by several asexual propagation procedures, including bulb scale propagation, natural propagation from bulblets and division, and by tissue culture originating from bulb scales. Propagation by these methods carried on through several successive generations has demonstrated that the novel and distinctive characteristics of this plant are fixed and hold true from generation to generation.

My study of this new plant has demonstrated that its clones retain the unusually large flower size, early bud coloration, and broad leaves when forced into flower out-of-season, which can be done from bulbs which have been dug at the proper stage of maturity and properly precooled, with a reliable performance, even during periods of relatively low light.

DESCRIPTION OF THE DRAWING

My new variety of lily plant is illustrated by the accompanying photographic drawing which, in the upper view, shows the distinctive broad leaf, mid-height silhouette of the plant with first opening flowers and a succession of buds on its relatively tall flowering stems; and the lower view shows a face view of a fully opened flower illustrating its bowl-shaped form and its broad, pure white inner tepals, together with a bud just prior to opening, the color rendition being as nearly true as can be reasonably obtained by conventional photographic procedures.

DESCRIPTION OF THE NEW VARIETY

The following is a detailed description of my new variety of Oriental hybrid lily with nomenclature according to The International Lily Register (The Royal Horticultural Society, London, 1969) and with color designations according to The R.H.S. Colour Chart published in 1966. These observations were made on field grown plants at Arcata, Calif., in the summer of 1985.

THE PLANT

Origin: Seedling.

Parentage: Unknown.

Classification:

*Botanic.*—Hybrid Lilium Cultivar; Division VII-B of The Horticultural Classification of Lilies by The Royal Horticultural Society.

*Commercial.*—Oriental Hybrid Lily.

Form: Single stem; erect, tall and bushy.

Height: 50 to 100 cm.

Growth: Vigorous, compact and sturdy with good strength.

Foliage:

*Quantity.*—Abundant.

*Leaf size.*—Ranging from about 10 cm. long and 2 cm. wide at the top of the stem down to 5 cm. long and 2 cm. wide at the bottom where the foliage growth begins.

*Leaf shape.*—Broad lanceolate with acuminate tip.

*Texture.*—Leathery.

*Aspect.*—Glossy.

*Color.*—Dark green to medium plum (chlorophyll pigmentation overlaid with anthocyanin).

Bulbs:

*Size.*—Varying, depending upon age, up to about 30 cm. in circumference.

*Color.*—White, with flushes of soft pink or yellow which deepen as the bulb becomes larger or is exposed to light.

THE BUD

Form: Ovate with acuminate tip.

Size: Averages about 12 to 15 cm. long and about 10 cm. in circumference depending upon light and nutritional levels.

Opening rate: The bud opens slowly, in response to morning light, and the buds open successively from the lowermost to the uppermost as is typical of Lilium.

Color: The buds are basically white with a slight suffusion of soft green or cream and the lower 5 cm. of the bud shows a soft flush of pale pink along the tepal midribs while the upper 5 cm. of the bud shows a soft green along the midribs.

Peduncle:

*Length.*—About 1 to 2 cm. and dark green in color. The peduncle may elongate under low light conditions or when the bulbs have been improperly stored prior to forcing.

THE FLOWER

Blooming habit: This plant flowers once and profusely in midseason for Oriental lilies, generally in late July under field conditions at Arcata, Calif. When properly forced from appropriately precooled bulbs, this plant will flower in 95 to 110 days in greenhouse.

Size: Large; averaging about 20 to 22 cm. in diameter, the tepals recurving to provide a bloom of about 16 to 18 cm. wide.

Borne: As a compact raceme on a strong, tall stem with each pedicel bearing one bud.

Shape: Bowl-shaped with broad tepals in hexagonal arrangement and slightly recurved.

Tepalage:

*Number.*—Six.

*Form.*—Ovate with the inner tepals averaging about 6 cm. wide and the outer tepals averaging about 3 cm. wide. The inner tepals overlap slightly at their base end.

*Color.*—The basic color is pure white and the tepals are heavily papillated. However, the papillae are also white. The nectaries are green.

*Color change.*—There is generally very little color change. Under cool conditions, a slight pink suffusion may appear.

*Papillae.*—Copious papillae in the center 12 cm. of each flower and pure white in color.

*Tepal longevity.*—The tepals stay on the stem about two to three weeks.

Pedicel:

*Length.*—About 6 to 8 cm.

*Color.*—Dark green.

*Character.*—Ascending at a 45° angle from the stem.

Disease resistance: The flower and the plant are adequately resistant to disease as observed in western Oregon and northwestern California.

Fragrance: The fragrance is heavy and sweet.

Lasting quality: The flower is long lasting, both on field grown plants and on forced potted cultivars.

REPRODUCTIVE ORGANS

Stamens:

*Number.*—Six.

*Arrangement.*—Typical of Lilium.

Anthers:

*Length.*—About 2.8 cm.

*Color.*—Greyed-Orange, 172B.

Filaments:

*Length.*—About 7 to 8 cm.

*Color.*—Soft white to soft green.

Pistil:

*Number.*—One per flower.

Style:

*Color.*—Light greeen to white, sometimes slightly pink.

Stigma:

*Size.*—6 mm. wide.

*Color.*—Soft purple-grey.

Ovary: Typical of Lilium.

I claim:

1. A new and distinct variety of Oriental hybrid lily, substantially as herein shown and described, characterized particularly by its pure white, unusually large flowers of excellent substance and broad tepalled form, borne on strong, plum-colored stems which have abundant foliage comprising broad leaves of dark green color.

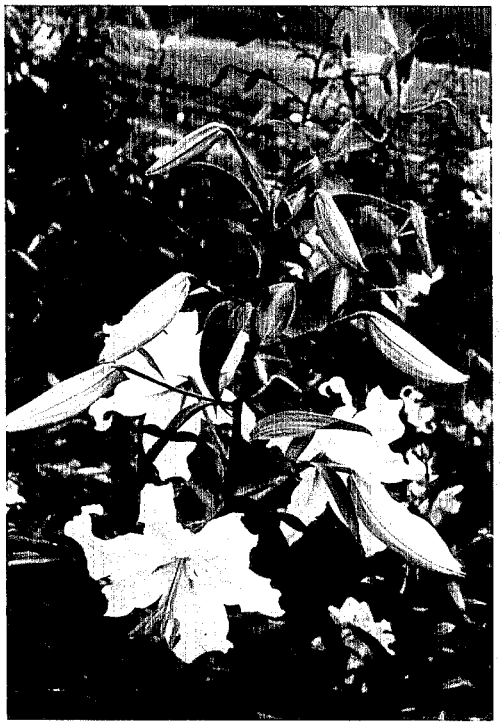
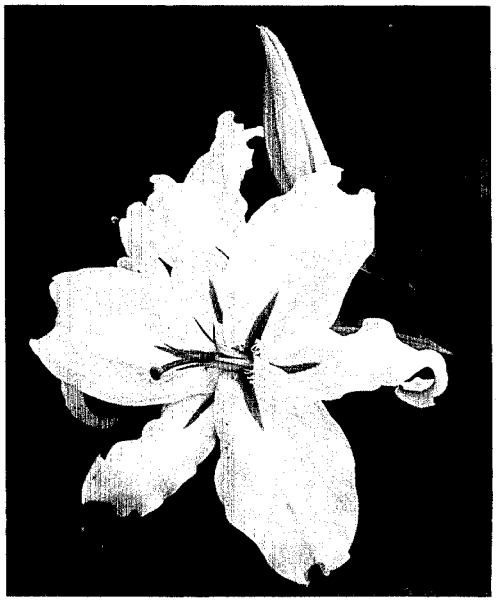

* * * * *